(12) United States Patent
Chien

(10) Patent No.: US 7,038,472 B1
(45) Date of Patent: May 2, 2006

(54) METHODS AND SYSTEMS FOR MEASURING INTERNAL DIMENSIONS OF MICROSCALE STRUCTURES

(75) Inventor: Ring-Ling Chien, San Jose, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 0 days.

(21) Appl. No.: 10/435,937

(22) Filed: May 12, 2003

(51) Int. Cl.
*G01R 27/08* (2006.01)
(52) U.S. Cl. .................................. 324/716; 324/691
(58) Field of Classification Search ............. 324/699, 324/716, 691, 525, 526; 73/864.01
See application file for complete search history.

(56) References Cited

U.S. PATENT DOCUMENTS

| | | | |
|---|---|---|---|
| 4,871,962 A | * | 10/1989 | Cheung ..................... 324/699 |
| 5,965,410 A | | 10/1999 | Chow et al. |
| 6,485,690 B1 | | 11/2002 | Pfost et al. |
| 6,500,323 B1 | | 12/2002 | Chow et al. |
| 6,537,771 B1 | | 3/2003 | Farinas et al. |
| 6,558,960 B1 | | 5/2003 | Parce et al. |
| 6,589,729 B1 | | 7/2003 | Chan et al. |
| 6,630,353 B1 | | 10/2003 | Parce et al. |
| 6,670,153 B1 | | 12/2003 | Stern |
| 6,681,616 B1 | | 1/2004 | Spaid et al. |

* cited by examiner

*Primary Examiner*—Vincent Q. Nguyen
(74) *Attorney, Agent, or Firm*—Donald R. McKenna; Ann C. Petersen

(57) ABSTRACT

The present invention provides novel devices for measuring internal dimensions of microscale structures. Methods in accordance with the invention use the voltage measured at a midpoint between a reference structure and a sample structure to determine the resistance of the sample structure, and to then calculate an internal dimension of the sample structure.

11 Claims, 3 Drawing Sheets

METHODS AND SYSTEMS FOR MEASURING INTERNAL DIMENSIONS OF MICROSCALE STRUCTURES

BACKGROUND OF THE INVENTION

A vast majority of analytical instrumentation employs tubular structures for various purposes. Some of the common examples are columns for chromatographic uses, and capillaries used in capillary electrophoresis. In recent years the scientific community has advanced analytical instrumentation technology greatly by miniaturizing laboratory analyses that in the past required large instruments and lengthy procedures. One of the technologies that has accompanied these miniaturizing efforts, microfluidic technology, has brought with it a new set of challenges for the scientist. One such challenge is the ability to transfer precise aliquots of fluid materials through channels of microscale dimensions.

Examples of tubular structures used in microfluidic technology are the capillaries or pipettors used to introduce remotely stored reagents into a microfluidic device. These capillaries or pipettors may be used in high throughput devices employing microfluidic technology, which typically store the chemical reagents and sample materials used in the microfluidic device in an external storage system. Depending on the application being performed on the microfluidic device, the reagents or samples may be introduced into the microfluidic device in a continuous flow format or at frequent intervals.

The dimensions of tubular structures used in conjunction with microfluidic devices are generally quite small. The dimensions of a tubular structure often play a significant role in the usefulness of that structure for a particular application. For example, the inner diameter of a capillary used to introduce regents onto a microfluidic device determines the volume of the aliquots of materials being introduced into the device.

Similarly, the dimensions of the channels in microfluidic devices are also quite small. The dimensions of the channels also often play a significant role in the usefulness of that structure for a particular application. For example, the internal dimensions a microfluidic channel have a strong influence on the characteristics of the fluid flow through that channel.

Conventional methods of determining the internal diameter of a tube having microscale dimensions or the internal dimensions of a microfluidic channel are imprecise and time consuming. The present invention provides methods and systems for the rapid and precise measurement of the internal diameter of a microscale tube or channel.

BRIEF SUMMARY OF THE INVENTION

The present invention deals with the measurement of internal dimensions of microscale structures by determining the electrical resistance of a fluid contained within the structure and comparing it with the electrical resistance of the same fluid contained within a reference structure.

In a first aspect, the present invention provides a method for measuring an internal diameter of a tube with a circular cross section by providing a reference tube having a known internal diameter and length, fluidly connecting a sample tube having an unknown diameter and a known length to the reference tube, and flowing a fluid through the reference and sample tubes. A voltage potential is then applied across the reference and sample tubes and voltage at a location between the two is measured. Since the electrical current generated by the voltage potential will be the same in both the reference and sample tubes, the measured voltage across each of the tubes will be proportional to the electrical resistance across each of the tubes. Accordingly, the ratio of the voltages across the two tubes can be used to determine the ratio of electrical resistances across the two tubes, which can then be used to determine the ratio of the internal diameters of the two tubes.

In another aspect, the present invention provides a highly precise method for measuring the internal diameter of a tube by relying on the principle underlying a Wheatstone bridge circuit. Methods in accordance with this aspect comprise the steps of providing a reference capillary having a known resistance when filled with a particular fluid, fluidly coupling the reference capillary to a sample capillary having an unknown resistance when filled with the same fluid, and coupling two resistors with the reference and sample capillaries to form a Wheatstone bridge circuit, and flowing the fluid through the reference and sample capillaries. The method further comprises applying a voltage potential through the circuit and measuring the voltage across the bridge. Finally, the resistance of the sample capillary is determined based on the voltage measured across the bridge.

In other aspects of the invention, internal dimensions of structures that do not have circular cross sections can be determined. For example, the width of a rectangular channel on a microfluidic device can be determined by employing methods in accordance with the invention.

In one embodiment, the methods of the invention further utilize reference and sample capillaries having an internal diameter within about 1 µm to about 100 µm.

DETAILED DESCRIPTION

Figure 1:
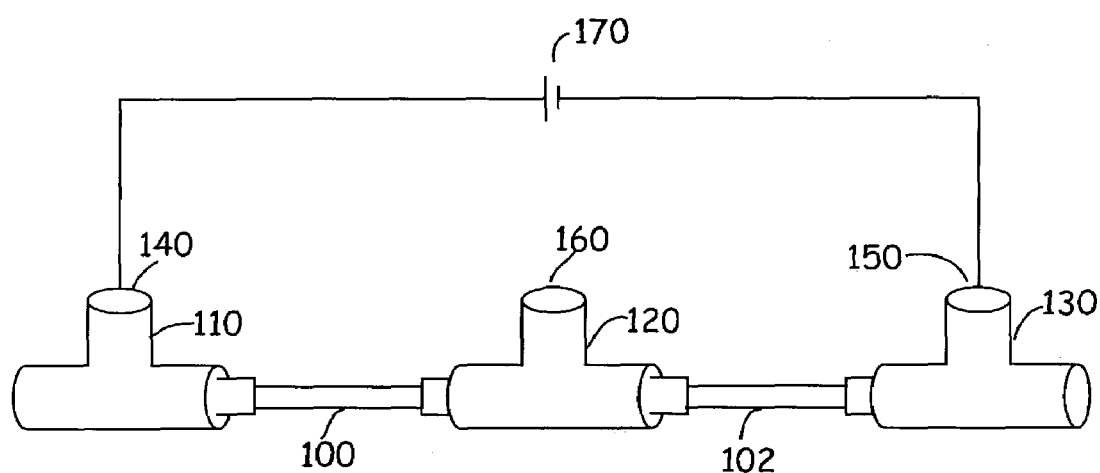
FIG. 1 illustrates a schematic of an apparatus used to serially connect sample and reference tubes for performing methods in accordance with the present invention.

The present invention enables precise measurements of internal dimensions of microscale structures. Such structures appear in high throughput microfluidic screening systems as pipettors comprising microscale conduits (tubes, capillaries or channels) that introduce samples into a microfluidic device from an external source or as channels in a microfluidic device. The microfluidic devices typically comprise networks of microscale channels fluidly connected to the pipettors as well as integrated reservoirs. As used herein, the term "microscale" generally refers to structural elements or features of a device that has at least one fabricated dimension in the range of about 0.1 µm and about 500 µm. When used to describe a fluidic element, such as a conduit, channel or capillary, the terms "microscale" or "microfluidic" generally refer to one or more fluid passages, chambers or tubes which have at least one internal cross-sectional dimension, such as depth, width, length, or diameter, that is less than 500 µm, and typically between about 0.1 µm and about 500 µm, more preferably between about 0.1 µm and 200 µm and often between about 0.5 µm and 100 µm. Microfluidic devices and their manufacture are described in U.S. Pat. Nos. 5,498,392, 5,779,868 and published patent application WO96/04547, each of which is incorporated in its entirety herein.

The methods of the invention can be used for measuring the diameter of tubular structures with circular cross sections that have a diameter in the range of about 5 μm to about 2000 μm. In preferred aspects, the methods of the invention are used to measure the diameter of tubes with a diameter in the range of about 10 μm to about 500 μm. In more preferred aspects, the methods are used to measure the diameter of tubes having an internal diameter in the range of about 10 μm to about 100 μm.

During the operation of a typical high throughput microfluidic screening system, fluidic materials stored remotely in an external storage system such as a multiwell plate or a micro titer plate are transported from the external storage system onto a microfluidic device via a capillary element by aspirating material from the external storage system into the capillary and drawing the material through the capillary and into a channel disposed on the microfluidic device. In some embodiments, buffer is also aspirated into the capillary element to separate aliquots of different materials. Generally, the quantity of a material delivered into the microfluidic device is controlled by controlling the time and the rate of aspiration of the material into the capillary. Since the rate of aspiration is a function of the internal diameter of the capillary, the volume of the aliquot of the material delivered into the microfluidic device depends on the internal diameter of the capillary. Therefore it is important to have the means for determining internal diameters of capillary elements with a high level of precision. Some of the common methods for measuring the internal diameter of a capillary include optical measurements and measurements of flow under constant pressure. Each of these methods, however, presents inadequacies in either the accuracy of the measurement or the time consumed in the setting up of the equipment to perform the measurement.

The present invention provides methods and systems for a precise measurement of the internal diameter of tubular structures. In general, the methods and systems of the present invention rely on measurement of electrical resistance of a tubular structure filled with a fluid comprising a standard conductivity to determine the internal diameter of the structure. Typically, the electrical resistance of a tubular structure filled with a fluid will depend on several factors including temperature, fluid composition, conductivity of the fluid, and flow rate. The present invention overcomes the challenge of trying to control all the relevant factors by incorporating a reference or control measurement in the systems whereby the impact of variations in any of relevant factor is nullified.

In embodiments of the invention, taking the reference measurement comprises measuring the resistance of a fluid filling a cylindrical tube of known length and cross-sectional area. Those skilled in the art would recognize that the shape of the exterior of the tube is inconsequential to the practice of the invention because it is the dimensions of the interior of the tube that are being determined. The electrical resistance $R$ of a fluid of conductivity $\sigma$ contained within a cylindrical tube of internal radius $r$, which is one-half the diameter $d$ (i.e. $d=2r$), and length $L$ is:

$$R = \frac{L}{\sigma \pi r^2}. \qquad (1)$$

So, for a tube with a known internal radius, and hence a known internal diameter, one can easily compute the theoretical resistance of a fluid of known conductivity in the tube. So, for example, if the resistance $R_2$ of a cylindrical tube with an unknown internal radius $r_2$ were compared to the resistance $R_1$ of a cylindrical tube with a known radius $r_1$, and if both tubes are of the same length and are filled with the same liquid, the ratio of the measured resistances of the tubes is $$\frac{R_2}{R_1} = \frac{L_2 r_1^2}{L_1 r_2^2}. \qquad (2)$$

By taking the ratio of resistances, the conductivity of the solution drops out of the equation. This also effectively eliminates factors such as temperature, fluid composition, and flow rate from the calculation. By rearranging the ratio, the unknown internal radius $r_2$ can be computed from the measured resistances $R_1$ and $R_2$, and the known internal radius $r_1$:

$$r_2 = r_1 \cdot \sqrt{\frac{L_2 R_1}{L_1 R_2}}. \qquad (3)$$

If the two tubes are the same length, i.e. L1=L2, then equation (3) simplifies to $$r_2 = r_1 \cdot \sqrt{\frac{R_1}{R_2}}. \qquad (4)$$

Thus by measuring the electrical resistance of a fluid in a tube with an unknown radius and the resistance of the same fluid in tube with a known radius, where both tubes are of the same length, the unknown radius can be determined.

In methods in accordance with the present invention, the electrical resistance of a fluid filling a tube is determined by means of voltage measurements. In the embodiment shown in FIG. 1, a reference capillary 100 is serially connected to a sample capillary 102. The reference capillary has a known internal radius, and the reference and sample capillaries are of the same length. The reference and sample capillaries are connected by means of adapters 110, 120 and 130. Any suitable adaptor that forms a good fit with the diameter of the capillary or tube may be used. One example of an adaptor compatible with embodiments of the invention is a MICRO-TEE (Upchurch Scientific P/N P-775). A voltage controller and a power supply 170 are in electrical contact with the interior of adaptors 140 and 150. A voltage potential is applied across the fluid in adaptor 140 and the fluid in adaptor 150. The voltage between adaptors 140 and 150 produces an intermediate voltage at location 160, which is situated in between the reference capillary 100 and the sample capillary 102. For the purpose of illustrating the relationships between the voltage applied between adaptors 140 and 150 and the intermediate voltage, and to illustrate how those voltages are used to compute of the resistance of the reference and sample capillaries, the following designations are used:

$V_1$=voltage applied at location 140
$V_2$=voltage at location 150
$V_3$=voltage at location 160
$R_1$=electrical resistance of reference capillary 100, and
$R_2$=electrical resistance of sample capillary 102.

The electrical current generated by the voltage applied between adaptors 140 and 150, which in terms of the designations is $V_2-V_1$, is identical in both reference capillary 100 and sample capillary 102. Thus, the following relationship arises by equating the currents flowing through capillaries 100 and 102 after expressing the currents in terms of voltage and resistance using Ohm's law:

$$\frac{V_3 - V_1}{R_1} = \frac{V_2 - V_3}{R_2}. \tag{5}$$

Solving for the resistance, $R_2$ gives $$R_2 = \frac{V_2 - V_3}{V_3 - V_1} \cdot R_1. \tag{6}$$

This expression for the resistance $R_2$ of the sample capillary 102 can be substituted into equation (4) supra to express $r_2$ in terms of the measured voltages and $r_1$:

$$r_2 = r_1 \cdot \sqrt{\frac{V_3 - V_1}{V_2 - V_3}}. \tag{7}$$

Using this expression, the unknown internal radius $r_2$ of sample capillary 102 can be computed from the known internal radius $r_1$ of reference capillary 100, and the three measured voltages.

The embodiment shown in FIG. 1 could also employ reference and sample tubes of different lengths. If, for example, the sample tube 102 and reference tube 100 in FIG. 1 had respective lengths $L_2$ and $L_1$, the expression relating internal radius $r_2$ to the tube lengths and voltages could be obtained by substituting the value of $R_2$ from equation (6) into equation (3):

$$r_2 = r_1 \cdot \sqrt{\frac{(V_3 - V_1)L_2}{(V_2 - V_3)L_1}}. \tag{8}$$

Accordingly, the unknown internal radius $r_2$ of the sample capillary 102 in FIG. 1 could be determined by measuring the lengths of the sample 102 and reference 100 capillaries, and the voltages between the fluid in adaptors 140, 150, and 160.

Wheatstone Bridge Circuit

In a related aspect, embodiments of the invention employ a Wheatstone bridge circuit to measure the resistance of the sample tube and thereby determine the internal diameter of the sample tube. The sample tube resistance is determined by forming a Wheatstone bridge circuit using two known resistances, a reference tube, and the sample tube.

Figure 2A:
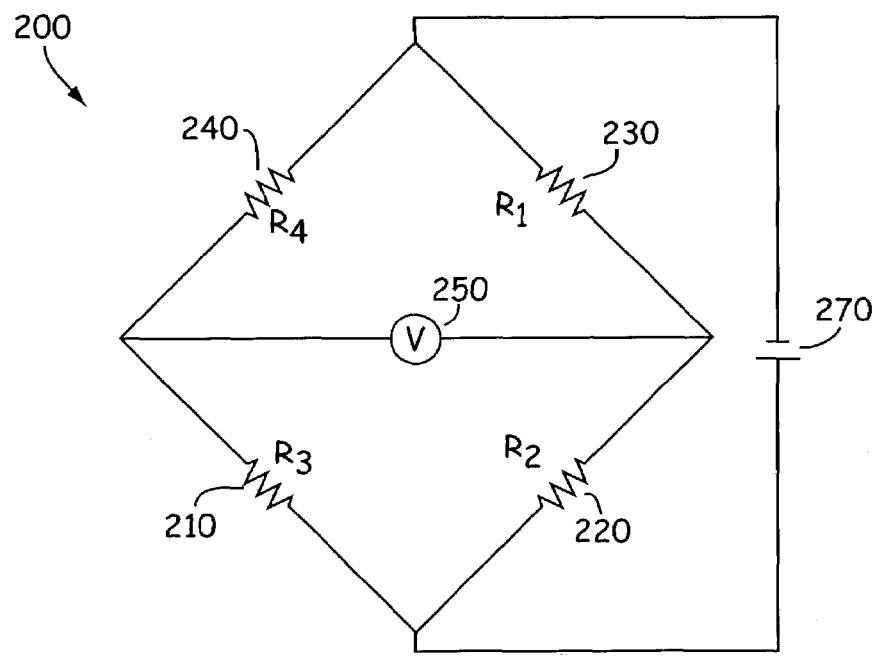
FIGS. 2A and 2B illustrate an embodiment employing a Wheatstone bridge circuit.

A Wheatstone bridge is a commonly used divided bridge circuit used to measure electrical resistance. Because of their outstanding sensitivity, Wheatstone bridge circuits are commonplace in electrical instrumentation. A Wheatstone bridge circuit in accordance with the invention is shown in FIG. 2A. The circuit 200 comprises four resistors 210,220,230,240 arranged in a diamond orientation. A power supply 270 applies an input DC voltage, or excitation voltage, between the top and bottom of the diamond. The diamond arrangement of the four resistors creates two current paths, each current path traversing two resistors. One current path contains resistors 210 and 240, while the other path contains resistors 220 and 230. An output voltage can be measured between the intersection of the two resistors in one path and the intersection of the two resistors in the other path. When the output voltage 250 is zero, the bridge is balanced. When there is a change in resistance of one of the two paths the balanced bridge becomes unbalanced, causing the output voltage to have a non-zero value. The bridge can be rebalanced, which will bring the output voltage back to zero, by adjusting the resistance in the other path to compensate for the change in resistance.

Embodiments of the present invention employ a Wheatstone bridge comprising a source of electrical current that produces an electrical current in the two current paths of the bridge, and a voltmeter or galvanometer 250 for measuring the output voltage or a current indicative of the output voltage respectively. In embodiments of the invention, the resistances of three of the four resistors 210,220,230,240 are known. Accordingly, one current path contains one resistor with a known resistance and one resistor with an unknown resistance, while the second current path two resistors with known resistances. In order to determine the resistance of the unknown resistor, the resistances of one or more of the other three resistors is adjusted until the voltage across the voltmeter or galvanometer 250 decreases to zero, indicating a zero output voltage and hence a balanced bridge.

Figure 2B:
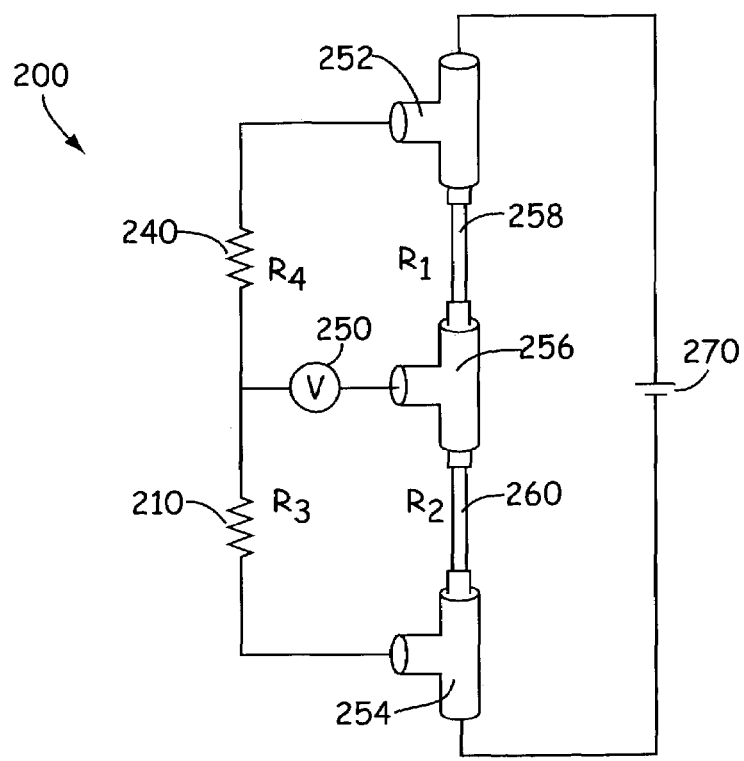

FIG. 2B shows, for an embodiment of the invention, the physical components that form the circuit in FIG. 2A. The Wheatstone bridge in the embodiment of FIG. 2B comprises two resistors 210,240, and a reference tube 260 and a sample tube 258. At least one of resistors 210,240 is adjustable. The resistances of the fluids contained in tubes 260 and 258 respectively correspond to resistors 220 and 230 in the circuit of FIG. 2A. The resistance of the resistors 210 and 240 are designated $R_3$ and $R_4$ respectively, the resistance of the reference tube 258 is designated $R_1$, and the resistance of the sample tube 260 is designated $R_2$. A power supply 270 is used to apply a DC voltage to the bridge 200, and a voltmeter or galvanometer 250 is used to measure the voltage or current across the bridge 200. As is well known to those in the art, when the bridge 200 is balanced, which occurs when the voltage or current measured by the voltmeter or galvanometer 250 is zero, the resistance $R_2$ of the sample tube is $$R_2 = R_1 \frac{R_4}{R_3}. \tag{9}$$

So the ratio between the resistance $R_1$ of the reference tube 258 and the resistance $R_2$ of the sample tube 260 is $$\frac{R_1}{R_2} = \frac{R_3}{R_4}. \tag{10}$$

This ratio can be substituted into equation (4) in order to provide an expression that puts the unknown radius $r_2$ of the sample tube 260 in terms of the resistances ($R_3$ and $R_4$) of the resistors 210 and 240 and the known radius $r_1$ of the reference tube 258:

$$r_2 = r_1 \cdot \sqrt{\frac{R_3}{R_4}}. \qquad (11)$$

Therefore, the unknown radius $r_2$ of the sample tube 260 can be determined by placing the sample tube 260 in the same current path of a Wheatstone bridge as a reference tube 258 of known radius $r_1$, balancing the bridge by adjusting the voltage or current measured by the voltmeter or galvanometer 250 is zero, and by determining the resistance values $R_3$ and $R_4$ of resistors 210 and 240.

The reliability and accuracy of the methods of the present invention are confirmed by comparing the theoretical voltages derived from equation (1) and Ohm's law with the voltages measured in the embodiment of FIG. 1. Sample capillaries with lengths of 40.02, 40.42, 40.81, and 42.03 mm are placed, one at a time, into the embodiment of FIG. 1. The reference capillary has a length of 40.00 mm, and has the same inner radius as each of the sample capillaries (0.01 mm). The electrolyte solution in the vials and the interior of the capillaries comprises a conductivity buffer with a conductivity of 100,000 microSiemens/cm (Fisher Scientific, Catalog No. 09-328-5). Under these conditions, as can be calculated from equation (1), the electrical resistance in the reference capillary is 12.7 MΩ.

For each experiment, the same magnitude electrical current was flowed through the device shown in FIG. 1. This was accomplished by inserting platinum electrodes into the vials and applying a voltage gradient across the sample and reference capillary. Equation (1) and Ohm's law indicate that when the current, tube inner diameter, and fluid conductivity are constant, the voltage across the reference and sample tubes will vary with the combined length of those tubes. In the following table the theoretical voltages for a given current, which were calculated by substituting the combined length of the reference and sample tubes into equation (1) and Ohm's law, are compared to the experimentally measured voltages.

| Sample Capillary Length (mm) | $V_{theoretical}(V)$ | $V_{experimental}(V)$ | $V_{experimental}$ Std deviation (V) |
|---|---|---|---|
| 40.02 | 350 | 350.03 | 0.09 |
| 40.02 | 350 | 349.80 | 0.19 |
| 40.42 | 350.75 | 350.86 | 0.21 |
| 40.42 | 350.75 | 350.24 | 0.19 |
| 40.81 | 351.48 | 351.70 | 0.13 |
| 40.81 | 351.48 | 351.51 | 0.20 |
| 40.81 | 351.48 | 351.48 | 0.05 |
| 42.03 | 353.67 | 353.57 | 0.11 |
| 42.03 | 353.67 | 352.80 | 0.074 |

These results indicate that the measured voltages are accurate to within 0.3%, and also very precise.

Embodiments of the invention may also be applied to channels that do not have a circular cross section. For example, the width of a channel in a microfluidic device can be measured using methods in accordance with the present invention. Unlike the tubes with circular cross sections in the previously described embodiments, the channels in many microfluidic devices have an approximately rectangular cross-section. A more general form of equation (1), which applies to any tube or channel regardless of the shape of the internal cross-section of that tube or channel, is $$R = \frac{L}{\sigma A}, \qquad (12)$$

where A is the internal cross-sectional area of the tube or channel. In the case of a tube with a circular internal cross section $A = \pi r^2$, so equation (12) reduces to equation (1). In the case of a channel with a rectangular cross section, equation (12) becomes $$R = \frac{L}{\sigma w d}, \qquad (13)$$

where w is the width of the channel and d is the depth of the channel.

Figure 3A:
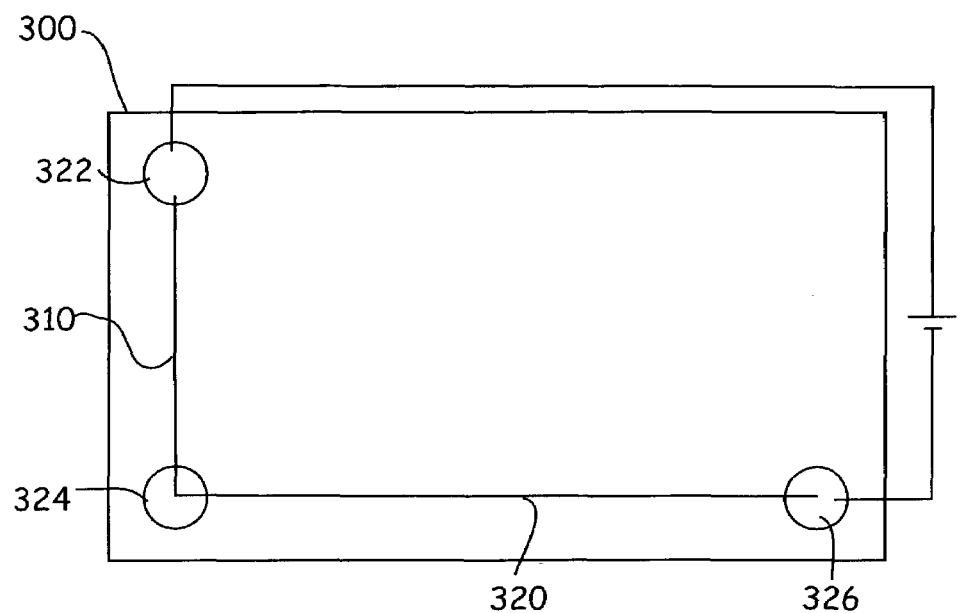
FIGS. 3A and 3B illustrate an embodiment in which the width of a microfluidic device channel is determined.

A schematic of a typical microfluidic device for measuring the effective channel diameter of a sample channel is shown in FIG. 3A. As shown in FIG. 3A, the device has a reference channel 310 having a known effective diameter, and a sample channel 320. Reference channel 310 is connected to the sample channel 320 via reservoir 324. An electrolyte solution is added into one or more of the reservoirs 322,324,326 so it flows into the channels 310,320. Electrodes are inserted into reservoirs 322 and 326 so a voltage potential can be applied across channels 310 and 320. An intermediate voltage is measured at reservoir 324. For the purpose of relating the applied voltage and measured voltage to the dimensions of the channels 310 and 320, the following designations are used:

$V_1$=voltage applied at location 322
$V_2$=voltage at location 326
$V_3$=voltage at location 324
$R_1$=electrical resistance of reference capillary 310
$R_2$=electrical resistance of sample capillary 320
$w_1$=width of reference capillary 310
$w_2$=width of sample capillary 320
$L_1$=length of reference capillary 310
$L_2$=length of sample capillary 320

In this embodiment, the depth d and the length L of the reference 310 and sample 320 capillaries are the same. Since in the embodiment of FIG. 3A the current through the reference capillary 310 and sample capillary will be the same, Ohm's law indicates that $$\frac{V_3 - V_1}{R_1} = \frac{V_2 - V_3}{R_2}. \qquad (14)$$

This equation is identical to equation (5). Substituting the expressions for $R_1$ and $R_2$ from equation (13) into equation (14), and solving for $W_2$ gives $$w_2 = w_1 \left( \frac{V_3 - V_1}{V_2 - V_3} \right) \qquad (15)$$

An experiment employing the embodiment shown in FIG. 3A was carried out on four different microfluidic devices. Each device had the channel layout shown in FIG. 3A, but the sample channel widths in the four devices were different.

The dimensions of all the other structures in the four devices were the same. The dimensions of the four devices were:

Reference Channel: 8.4 mm length, 40 µm width, 5 µm depth
Sample Channel: Device #1  8.4 mm length, 38 µm width, 5 µm depth
Device #2  8.4 mm length, 39 µm width, 5 µm depth
Device #3  8.4 mm length, 40 µm width, 5 µm depth
Device #4  8.4 mm length, 42 µm width, 5 µm depth To carry out the experiment, a DC voltage of 600V was applied to reservoir 322, and a DC voltage of 200 V was applied to reservoir 326. The electrolyte solution was 800 mM HEPES buffer at pH 7.5.

Figure 3B:
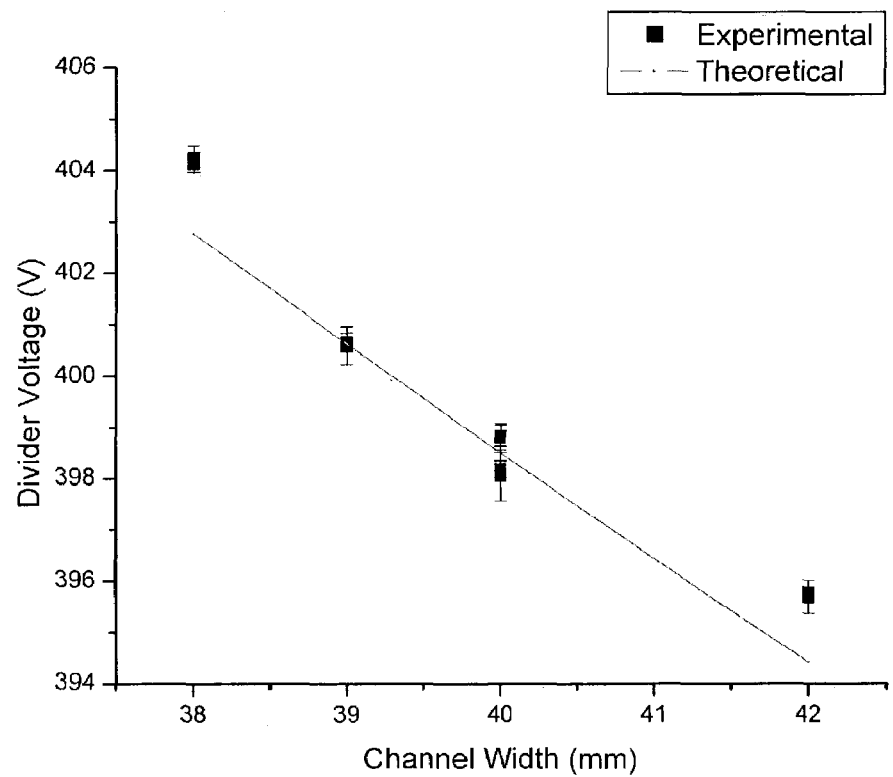

The results of the experiment are shown in FIG. 3B. As shown in FIG. 3B, the measured channel width correlates very closely to the theoretical channel width calculated from equation (15).

Although the present invention has been described in some detail by way of illustration and example for purposes of clarity and understanding, it will be apparent that certain changes and modifications may be practiced within the scope of the appended claims. All publications, patents and patent applications referenced herein are hereby incorporated by reference in their entirety for all purposes as if each such publication, patent or patent application had been individually indicated to be incorporated by reference.

What is claimed is:

1. A method of measuring an internal dimension of a sample structure comprising:
   providing a reference structure having a known internal dimension and a known length;
   serially connecting a sample structure having an unknown internal dimension and known length to said reference structure;
   flowing a fluid through said reference structure and said sample structure, the fluid flowing through the reference and sample structure forming a first conductive path;
   measuring a first voltage difference across the first conductive path;
   measuring a second voltage difference across a portion of the first conductive path spanning the length of the sample structure; and
   determining the internal dimension of said sample structure from the first voltage difference and the second voltage difference.

2. The method of claim 1, wherein the reference structure and sample structure are tubes with circular interior cross sections.

3. The method of claim 1, wherein the reference structure and sample structure are channels with rectangular interior cross sections.

4. The method of claim 1, wherein the reference structure and sample structure are of the same length.

5. The method of claim 1, wherein the reference structure and sample structure are of different lengths.

6. The method of claim 1, wherein the determining step comprises calculating a ratio of an electrical resistance of a portion of the first conductive path spanning said reference structure to an electrical resistance of the portion of the first conductive path spanning said sample structure.

7. The method of claim 1, wherein said reference structure comprises a capillary having an internal diameter within a range of about 1 µm to about 100 µm.

8. The method of claim 7, wherein said capillary has an internal diameter within a range of about 2 µm to about 50 µm.

9. The method of claim 7, wherein said capillary has an internal diameter equal to about 5 µm.

10. The method of claim 7, wherein said capillary has an internal diameter equal to about 10 µm.

11. The method of claim 7, wherein said capillary has an internal diameter equal to about 20 µm.

* * * * *